United States Patent
Kayyali et al.

(10) Patent No.: US 11,875,703 B2
(45) Date of Patent: *Jan. 16, 2024

(54) RENAL HILUM SURGICAL SIMULATION SYSTEM

(71) Applicant: Applied Medical Resources Corporation, Rancho Santa Margarita, CA (US)

(72) Inventors: Maya Kayyali, Irvine, CA (US); Gregory Hofstetter, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/155,935

(22) Filed: Jan. 18, 2023

(65) Prior Publication Data

US 2023/0154355 A1     May 18, 2023

Related U.S. Application Data

(63) Continuation of application No. 16/428,769, filed on May 31, 2019, now Pat. No. 11,587,465.

(60) Provisional application No. 62/791,450, filed on Jan. 11, 2019, provisional application No. 62/679,568, filed on Jun. 1, 2018.

(51) Int. Cl.
| | |
|---|---|
| *G09B 23/30* | (2006.01) |
| *G09B 23/28* | (2006.01) |
| *G09B 23/32* | (2006.01) |
| *A61B 1/313* | (2006.01) |

(52) U.S. Cl.
CPC ............. *G09B 23/30* (2013.01); *G09B 23/28* (2013.01); *G09B 23/32* (2013.01); *A61B 1/3132* (2013.01); *G09B 23/285* (2013.01)

(58) Field of Classification Search
CPC ....... G09B 23/28; G09B 23/30; G09B 23/303
See application file for complete search history.

(56) References Cited

U.S. PATENT DOCUMENTS

| | | | | |
|---|---|---|---|---|
| 7,575,434 | B2 * | 8/2009 | Palakodeti | G09B 23/28 434/267 |
| 9,548,002 | B2 * | 1/2017 | Black | G09B 23/285 |
| 10,818,201 | B2 * | 10/2020 | Hofstetter | G09B 23/30 |
| 11,158,212 | B2 * | 10/2021 | Hoke | G09B 23/28 |

(Continued)

FOREIGN PATENT DOCUMENTS

WO     WO 03/028978 A1     4/2003

OTHER PUBLICATIONS

European Patent Office, The International Search Report and Written Opinion for International Application No. PCT/US2019/035056, entitled "Renal Hilum Surgical System," dated Aug. 22, 2019, 13 pgs.

(Continued)

*Primary Examiner* — Kurt Fernstrom
(74) *Attorney, Agent, or Firm* — Thomas Nguyen; Patrick Ikehara

(57) ABSTRACT

A renal hilum surgical simulation system is provided. The renal hilum surgical simulation system includes simulated tissue layers and simulated renal organs and/or vasculatures. The renal hilum surgical simulation system is adapted for but not limited to laparoscopic donor nephrectomy surgical procedures.

20 Claims, 12 Drawing Sheets

(56) References Cited

U.S. PATENT DOCUMENTS

| | | | |
|---|---|---|---|
| 2008/0293026 A1* | 11/2008 | Senagore | G09B 23/285 434/262 |
| 2012/0015339 A1* | 1/2012 | Hendrickson | G09B 23/303 434/273 |
| 2012/0034587 A1* | 2/2012 | Toly | G09B 23/30 434/267 |
| 2014/0248596 A1 | 9/2014 | Hart et al. | |
| 2017/0148356 A1* | 5/2017 | Black | G09B 23/34 |
| 2018/0190155 A1* | 7/2018 | Segall | G09B 23/303 |
| 2019/0189032 A1* | 6/2019 | Fernandez | G09B 23/28 |

OTHER PUBLICATIONS

The International Bureau of WIPO, International Preliminary Report on Patentability for International Application No. PCT/US2019/035056, entitled "Renal Hilum Surgical Simulation Systems," dated Dec. 10, 2020, 8 pgs.

* cited by examiner

RENAL HILUM SURGICAL SIMULATION SYSTEM

CROSS-REFERENCE TO RELATED APPLICATIONS

This patent application is a continuation application of U.S. application Ser. No. 16/428,769, filed May 31, 2019, which claims benefit of U.S. Provisional Patent Application No. 62/679,568, filed on Jun. 1, 2018 and U.S. Provisional Patent Application No. 62/791,450, filed on Jan. 11, 2019, the disclosures of which are hereby incorporated by reference in their entirety.

BACKGROUND

This application relates to surgical training, and in particular, to simulated tissue structures and organ models for teaching and practicing various surgical techniques and procedures related but not limited to laparoscopic, endoscopic and minimally invasive surgery.

Laparoscopic surgery requires several small incisions in the abdomen for the insertion of trocars or small cylindrical tubes approximately 5 to 10 millimeters in diameter through which surgical instruments and a laparoscope are placed into the abdominal cavity. The laparoscope illuminates the surgical field and sends a magnified image from inside the body to a video monitor giving the surgeon a close-up view of the organs and tissues. The surgeon watches the live video feed and performs the operation by manipulating the surgical instruments placed through the trocars.

Kidney transplantation is the treatment of choice for patients with end-stage renal disease, which has rapidly increased in the last 10 years. There are currently 100,000 patients on the kidney transplant list, with many waiting 5-10 years for a kidney from a deceased donor. This has led to an increase in live donor nephrectomies, and in turn become a vital procedure for transplant surgeons to be proficient in to both minimize morbidity and mortality for the healthy donor, and to harvest the kidney in an optimal condition for transplantation. Laparoscopic donor nephrectomy (LDN) has since become the preferred surgical approach, as there are many advantages over open surgery, including decreased hospital stay, postoperative pain and morbidity, and increased donor satisfaction. However, while there are benefits to laparoscopic surgery, the complex surgical tasks involved place higher demands on the skills of the surgeon.

Simulation-based education has greatly enhanced laparoscopic surgical training by providing a safe and effective means for acquiring technical skills. However, despite the increased need for training on the LDN procedure, simulation training surgical simulation systems, simulators or models are lacking. As a result, trainees are limited to practicing the procedure in costly animal and cadaver labs or rely on experience gained through practice on patients in the operating room, which reduces operating room efficiency. To increase the safe conduct of the operation, increase the number of practitioners learning LDN, improve the skills of practitioners, reduce training costs and make training LDN easier, a LDN simulation model that focuses and isolates one or more of the most technically challenging steps in the operation, renal hilum dissection, is desirable and beneficial for reducing the learning curve of transplant trainees allowing them to achieve proficiency faster. In addition, a LDN-focused model or surgical simulation system would enable trainees to practice in a low-risk environment and potentially reduce the need, and associated costs, for animal and cadaver labs.

SUMMARY

In accordance with various embodiments of the present invention, a renal hilum surgical simulation system is provided. The surgical simulation system comprises a plurality of penetrable simulated tissue layers, a pocket disposed between the plurality of penetrable simulated tissue layers and encased by the peripheries of the plurality of penetrable simulated tissue layers, a plurality of fibrous layers disposed between the plurality of penetrable simulated tissue layers and at least one of a simulated renal organ and vasculature disposed between the plurality of fibrous layers and enclosed within the pocket.

In accordance with various embodiments, a renal hilum surgical simulation system is provided. The system in various embodiments comprises a first penetrable layer having an upper and lower surface and a second penetrable layer having an upper and lower surface. In various embodiments, the periphery of the upper surface of the second penetrable layer is connected to a periphery of the lower surface of the first penetrable layer and in various embodiments a pocket is disposed between the first and second penetrable layers. The pocket in various embodiments is delimited and encased by the peripheries of the first and second penetrable layers connected together. A plurality of fibrous layers in various embodiments are disposed between the first and second penetrable layers and in various embodiments at least one simulated renal vasculature is disposed between the plurality of fibrous layers and enclosed within the pocket.

In accordance with various embodiments, a renal hilum surgical simulation system comprises a first penetrable layer having an upper and lower surface and a second penetrable layer having an upper and lower surface. In various embodiments, a periphery of the upper surface of the second penetrable layer is connected to a periphery of the lower surface of the first penetrable layer and in various embodiments a pocket disposed between the first and second penetrable layers. The pocket in various embodiments is delimited and encased by the peripheries of the first and second penetrable layers connected together. A plurality of fibrous layers in various embodiments are disposed between the first and second penetrable layers and in various embodiments at least one simulated renal organ disposed between the plurality of fibrous layers and enclosed within the pocket.

In accordance with various embodiments, a renal hilum surgical simulation system comprises a first penetrable layer having an upper and lower surface and a second penetrable layer having an upper and lower surface. In various embodiments, a periphery of the upper surface of the second penetrable layer is connected to a periphery of the lower surface of the first penetrable layer and in various embodiments a pocket is disposed between the first and second penetrable layers. The pocket in various embodiments is delimited and encased by the peripheries of the first and second penetrable layers connected together and a plurality of fibrous layers in various embodiments are disposed between the first and second penetrable layers. A plurality of simulated renal vasculature in various embodiments are disposed between the plurality of fibrous layers and enclosed within the pocket and/or at least one simulated renal organ in various embodiments is disposed between the plurality of fibrous layers and enclosed within the pocket.

In accordance with various embodiments, a renal hilum surgical simulation system is provided and comprises a simulated renal vasculature and/or a simulated renal organ. In various embodiments, a renal hilum surgical simulation system is provided and comprises at least one fibrous layer, e.g., batting. In various embodiments, a renal hilum surgical simulation system or renal hilum laparoscopic donor nephrectomy surgical simulation system is provided. In various embodiments, a surgical simulation system is provided and comprises a simulated vasculature, a simulated organ, a simulated renal vasculature, a simulated renal organ and/or any combinations thereof and/or individually. In various embodiments, the system comprises a first penetrable layer having an upper and lower surface and a second penetrable layer having an upper and lower surface. In various embodiments, a periphery of the upper surface of the second penetrable layer is connected to a periphery of the lower surface of the first penetrable layer and in various embodiments, the first and second penetrable layers are made of silicone. A pocket in various embodiments is disposed between the first and second penetrable layers and in various embodiments, the pocket is delimited and encased by the peripheries of the first and second penetrable layers connected together. A top fibrous layer in various embodiments has an upper and lower surface and in various embodiments is disposed under the first penetrable layer with the lower surface of the first penetrable layer next to and in contact with the upper surface of the top fibrous layer. A bottom fibrous layer in various embodiments has an upper surface and a lower surface and in various embodiments is disposed above the second penetrable layer with the upper surface of the second penetrable layer next to and in contact with the lower surface of the bottom fibrous layer. A middle fibrous layer in various embodiments has an upper surface and a lower surface and in various embodiments is positioned between the top fibrous layer and the bottom fibrous layer. A first simulated renal vasculature in various embodiments is connected to upper surface of the bottom fibrous layer and the lower surface of the middle fibrous layer and in various embodiments, a second simulated renal vasculature is connected to the lower surface of the top fibrous layer and the upper surface of the middle fibrous layer. In various embodiments, the top, bottom and middle fibrous layers and the first and second simulated renal vasculatures are enclosed within the pocket.

Many of the attendant features of the present invention will be more readily appreciated as the same becomes better understood by reference to the foregoing and following description and considered in connection with the accompanying drawings.

BRIEF DESCRIPTION OF THE DRAWINGS

The present inventions may be understood by reference to the following description, taken in connection with the accompanying drawings in which the reference numerals designate like parts throughout the figures thereof.

DETAILED DESCRIPTION

In a LDN procedure, renal hilum dissection is one of the more challenging and high-risk steps due to the need to mobilize multiple critical structures. Currently, there is an unmet need for simulated models or surgical simulation systems that trainees can practice on to become proficient at this step of the operation. A simulated model or surgical simulation system of the renal hilum would reduce the learning curve by allowing surgical trainees to practice the required dissection repeatedly in a low-risk environment. To be effective, the surgical simulation system should allow for complete dissection of specific structures within the renal hilum from a laparoscopic approach, which includes one or more of the following simulated anatomy and landmarks to be present and identifiable in the model or surgical simulation system: kidney, adrenal gland, renal vein, renal artery, ureter, gonadal vein, adrenal vein, lumbar vein, and aorta. These structures should be anatomically correct and/or be made of materials that have a similar simulated tissue reaction encountered in the LDN procedure. In addition, these structures may be surrounded by simulated dissectible areolar tissue of appropriate density to provide realistic tactile feedback. Practice on the surgical simulation system can promote identification of the appropriate anatomy and acquisition of appropriate tissue handling and dissection skills required for the procedure.

The renal hilum surgical simulation system in accordance with various embodiments allows a trainee to focus on the skills necessary to practice the most challenging steps within a LDN procedure. To provide a realistic procedural training environment, in various embodiments, the surgical simulation system is positioned appropriately. To further enhance the training environment, the surgical simulation system uses simulated materials to represent the various anatomical landmarks as well as materials to simulate areas of dissectible tissue, which provide key visual and tactile feedback useful for the training of an LDN procedure. In order to simulate the tactile feel of the anatomical structures encountered during the LDN procedure, in accordance with various embodiments, specific combinations of materials, construction, and design have been chosen for various components found within the surgical simulation system.

Figure 1:
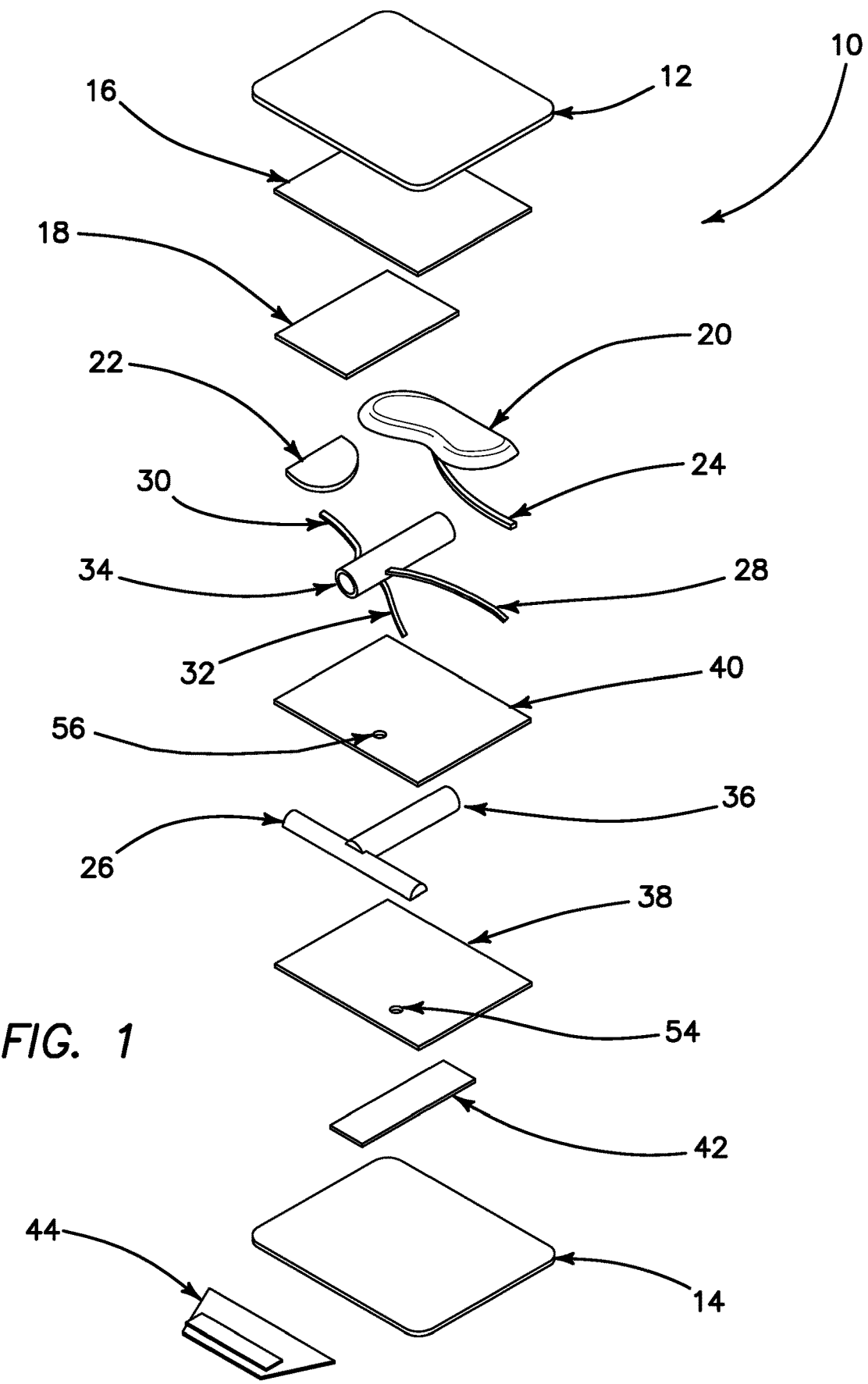
FIG. 1 is an exploded view of a renal hilum surgical simulation system in accordance with various embodiments of the present invention.

Turning now to FIG. 1, an exploded perspective view of a renal hilum surgical simulation model or system 10 according to various embodiments of the present invention is shown. The inner contents (anatomical structures and fibers) of the surgical simulation system 10 are encapsulated between two layers of silicone, a top penetrable layer 12 and a bottom penetrable layer 14, that are adhered together to create a closed pocket. Inside the pocket, the top outermost layer is a top fibrous layer 16 constructed of a simulated dissectible tissue area made of multiple layers of sheets of polyester fibers, e.g., batting, adhered using small amount of silicone or adhesive that the surgeon is to dissect or cut through in order to uncover and reach the anatomical structures encountered in the LDN procedure. This dissection area comprising of the multiple layers of polyester fibers, such as a half-fibrous layer 18, that are adhered together, fiber to fiber, e.g., batting to batting, as well as fiber, e.g., batting, to anatomical simulated structures are created to demonstrate the varying densities of the anatomy found in the body. In accordance with various embodiments, one or more of the layers are planar and/or stacked relative to each other.

In accordance with various embodiments, a layer of simulated anatomical landmarks is provided. The simulated anatomical landmarks in various embodiments comprise a simulated kidney 20, adrenal gland 22, ureter 24, and/or aorta 26. While none of these components should be dissected or cut during the simulated procedure, these landmarks are included in the surgical simulation system 10 to help orientate and/or educate the trainee. For example, the simulated ureter 24 should be identified but not touched, and is used as a tool to navigate to the location of the gonadal vein 28. Although the simulated landmarks should not be touched or manipulated by the trainee, one or more of these simulated anatomical structures includes one or more visual characteristics such as size, shape, color and/or any combination thereof, to simulate anatomy and/or to pose as indicators to allow for orientation within the simulated environment. In various embodiments, one or more of these simulated anatomical structures also comprises one or more tactile characteristics, such as texture, resiliency, elasticity and/or any combination thereof to further enhance identification of the simulated landmarks and/or as assessment and/or educational indicators. For example, in various embodiments, one or more of the simulated landmarks holds its shape until cut or excessively manipulated and thus if inadvertently cut or otherwise unduly manipulated, the simulated landmarks would reflect this treatment and thereby providing an assessment for an evaluator and/or educational indicator for a trainee.

During the simulated procedure, the simulated gonadal vein 28, adrenal vein 30, and lumbar vein 32 are located and circumferentially dissected, or skeletonized. During this skeletonization, the surgeon may pull up on the veins in order to make cuts and dissect through the fibers or batting. This is one of the most challenging steps in the procedure as the veins are very fragile and will break or tear if incised or if too much force is put on them. For surgeons to become comfortable or proficient in these steps of the procedure, they must understand the force required to manipulate the veins during dissection without harming them and thus the necessity to simulate the fragility of the veins.

In accordance with various embodiments, the simulated gonadal vein 28, adrenal vein 30, and/or lumbar vein 32 are made of a silicone or silicone foam that is molded into thin flat structures to simulate fragility of the various veins. It should be noted that gonadal, adrenal, and lumbar veins found within the human body are hollow cylindrical structures through which blood flows and have diameters of 3 mm, 4 mm, 2 mm respectively. As such, in accordance with various embodiments, while the simulated gonadal vein 28, adrenal vein 30, and/or lumbar vein 32 are not exact replicas of anatomy, e.g., in size and/or shape, these simulated veins are provided, for example, in size and/or shape along with the choice of material, e.g., silicone, to aid in the manufacturing process and replicate the tactile feel of the corresponding structures.

Figure 2:
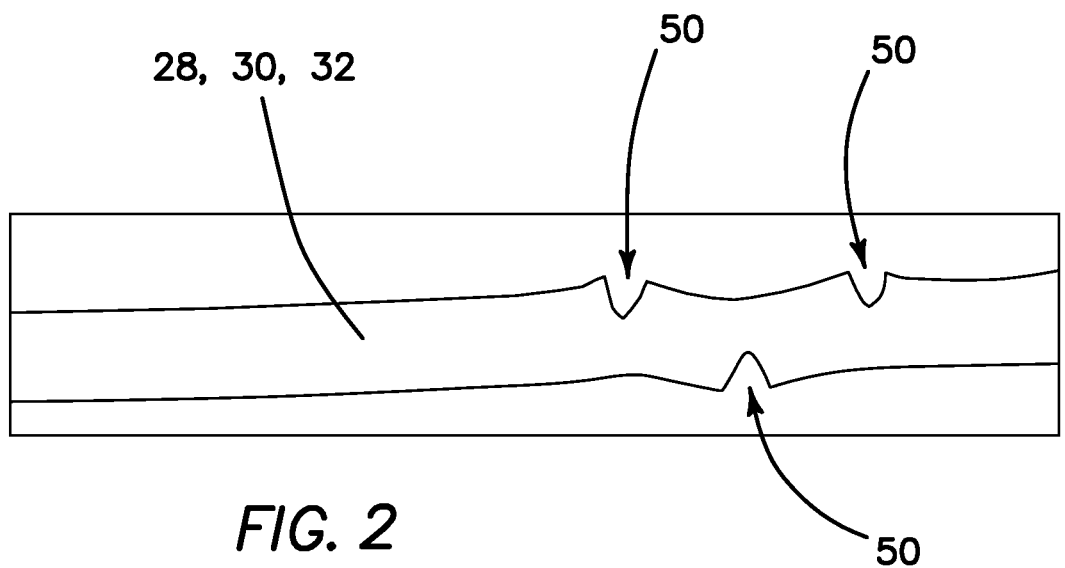
FIG. 2 is a top view of portions of the renal hilum surgical simulation system in accordance with various embodiments of the present invention.

In various embodiments, the simulated gonadal, adrenal, and lumbar veins, 28, 30, 32 includes one or more cuts or notches 50 along their lengths in predetermined locations as shown in FIG. 2. These predetermined notches 50 create weak or break points at specific locations, allowing the simulated vessels to simulate the fragility of such vessels. Additionally, in various embodiments, if excessive force or manipulation is applied to the simulated veins, the simulated veins will separate at one or more of the notches 50. A separated or torn vessel can provide an assessment and/or educational indication for or regarding the trainee's specific performance of or during the simulated procedure. Furthermore, the location of where the tear occurred, as indicated at a particular notch or weak point, can further assist in providing a more detailed assessment and/or educational indicator of the force or manipulation applied to the torn simulated vessel. It should however be noted that simulated vessels with predetermined notches may inhibit assessment of the simulated vessels after the procedure is performed, e.g., identifying new versus old or pre-installed notches may prove difficult, and as such predetermining the location and/or size of the notches or weak points can assist in reducing or eliminating this inhibition.

In various embodiments, the simulated lumbar vein within the surgical simulation system is under tension. The simulated lumbar vein, in various embodiments, is pulled taut and attached to the back of the model or surgical simulation system, putting it on tension. Placing the simulated lumbar vein under tension allows the simulated vein or portions thereof to snap when nicked or excessively tugged during circumferentially dissection. This snapping simulates or represents the fragility of the simulated lumbar vein as the amount of force used to snap the simulated vessel is similar to the amount of force to similarly affect a non-simulated lumbar vein.

In various embodiments, the surgical simulation system 10 comprises a simulated renal vein 34 and a simulated renal artery 36. The simulated renal vein 34 and renal artery 36 are separated from the surrounding fibers or batting (i.e. skeletonized) during the simulated procedure. The simulated renal vein 34 and renal artery 36 have much larger diameters (approximately 1.2 cm and 6 mm, respectively) than that of the simulated gonadal, adrenal, and lumbar veins 28, 30, 32 giving them more integrity and/or strength to simulate the tactile differences in the simulated renal vein 34 and renal artery 36.

Figure 3:
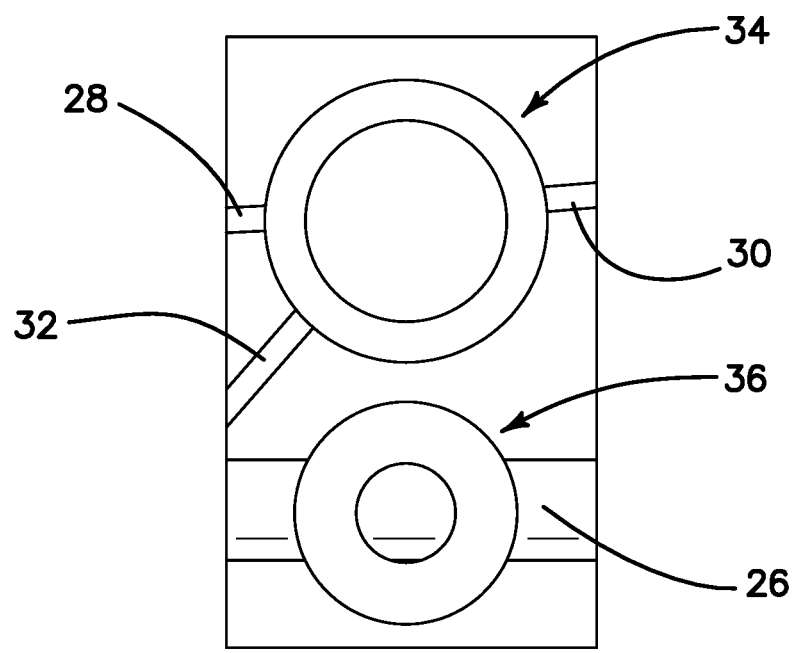
FIG. 3 is a cross-sectional view of a renal vein and artery in accordance with various embodiments of the present invention.

In accordance with various embodiments, with reference to FIG. 3, the illustrated simulated renal artery 36 has a smaller overall diameter but thicker wall relative to the simulated renal vein 34 having a larger diameter and thinner wall. In various embodiments, the simulated renal artery and vein are made of silicone and, in various embodiments, the simulated renal artery comprises a thick layer of silicone providing a thicker wall thickness of the simulated vessel. In various embodiments, the layer of silicone is made thicker by applying multiple thin layers or coats of wet or dry silicone. As a result of a thicker wall, the vessel will be harder to penetrate, i.e., the simulated renal artery is harder to penetrate versus the simulated renal vein. The simulated renal vein, in various embodiments, has a thin layer of silicone to provide a thin wall thickness. As a result, the vessel, e.g., the simulated renal vein, will be easier to puncture or nick.

Providing a contrast in structural integrity of the renal vein and renal artery further provides or enhances the simulation and/or the training and/or assessment indications as the tactile force allowed during the simulated procedure to circumferentially dissect around each of the structures without puncturing or otherwise unduly disrupting them is different for each vessel. In various embodiments, the thinner walls of renal vein 34 are fragile and/or made with a thinner layer of material. In contrast, in various embodiments, the simulated renal artery 36 is made of a thicker layer or layers of material. Both vessels are made of or molded from silicone and/or a similar fragile material that will hold its shape including conductive material.

In various embodiments, the simulated renal vein 34 and/or renal artery 36 are filled with fluid or the like to further mimic anatomy and/or for assessment or training indicators. For example, if either of the vasculature is punctured, fluid may be expelled or trickle out of the simulated vessels and thereby provide a visual indication of punctured vasculature and potentially indicating further training or decreased proficiency of the trainee.

Figure 4A:
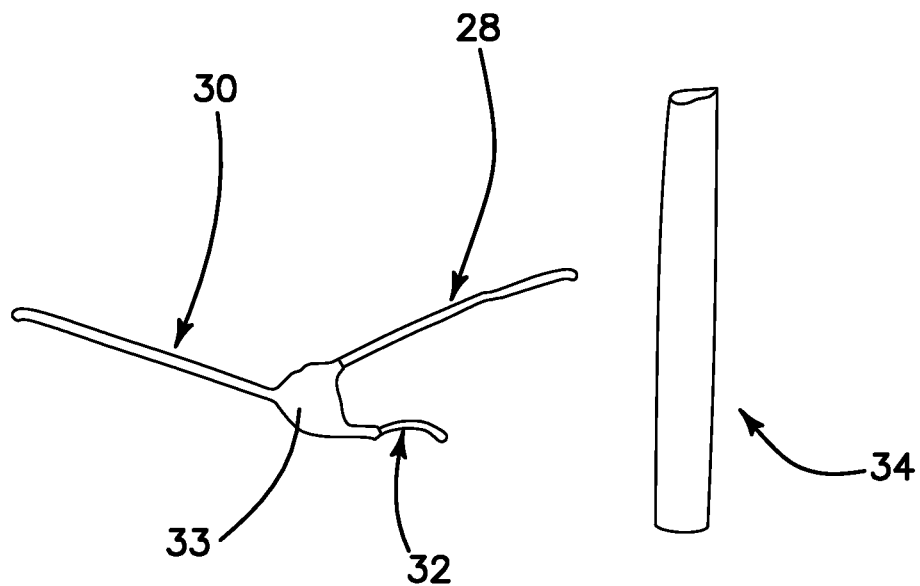
FIG. 4A is a side view of portions of the renal hilum surgical simulation system in accordance with various embodiments of the present invention.
Figure 4B:
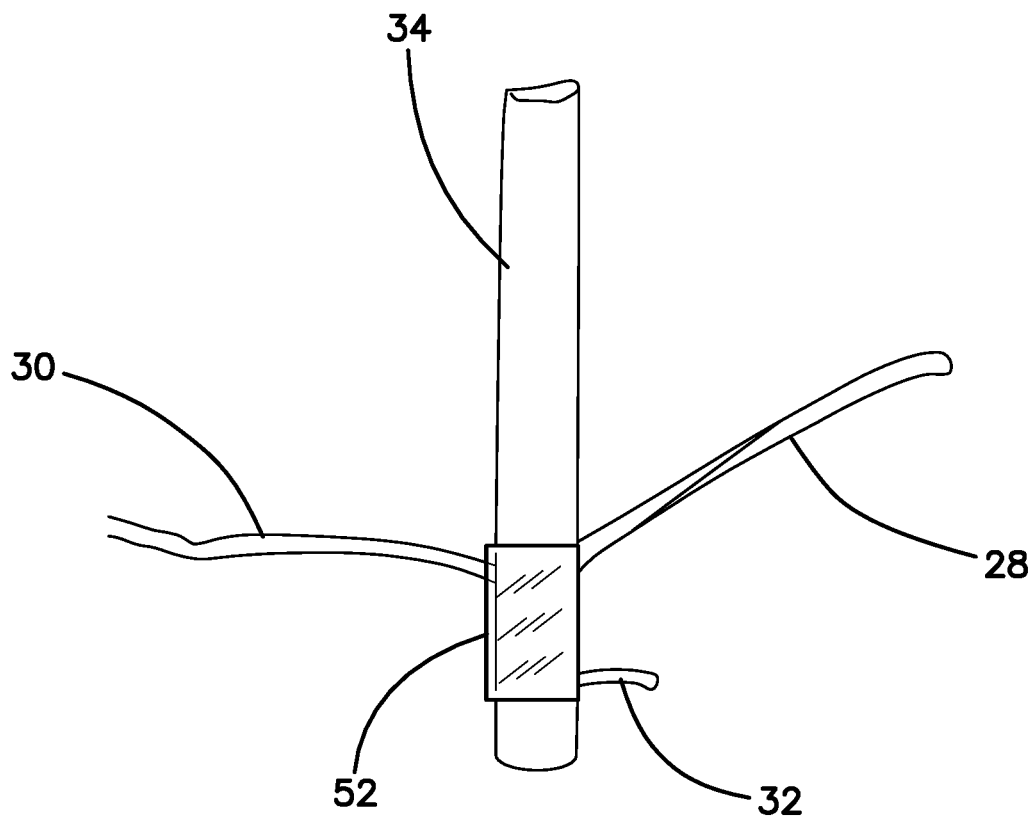
FIG. 4B is a top view of assembled portions of the renal hilum surgical simulation system in accordance with various embodiments of the present invention.

In FIGS. 4A-B, the simulated adrenal vein 30, gonadal vein 28, and lumbar vein 32 are adhered or otherwise attached to the simulated renal vein 34 at a renal vein adhesion area 52 and, in various embodiments, through adhesion of silicone to silicone. The renal vein adhesion area 52 is depicted by a rectangular box in FIG. 4B. Even though the adhesion area is depicted as a rectangular shape, the adhesion area may be any shape. The attachment area 52 is illustrated or referred throughout as a guide and as an exemplary way to show where the components are adhered or otherwise attached or where adhesive or the like is applied. In various embodiments, the simulated gonadal vein 28, adrenal vein 30, and lumbar vein 32, are molded separately and are minimally and/or weakly adhered to the renal vein 34 to increase the fragility of the simulated veins for, e.g., assessment and/or training, when the simulated vessel is put on tension and dissected around. The weak adhesion in various embodiments is achieved by using a weak adhesive or similar attachment, such as a silicone with a softer durometer, and/or removing connector 33 and attaching the simulated veins 28, 30, 32 directly to the simulated renal vein 34.

Figure 5A:
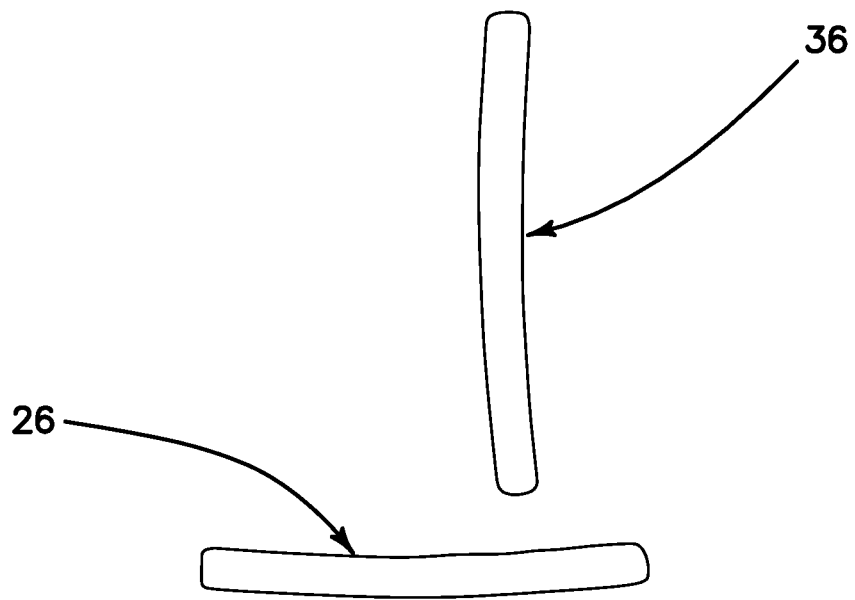
FIG. 5A is a top view of portions of the renal hilum surgical simulation system in accordance with various embodiments of the present invention.
Figure 5B:
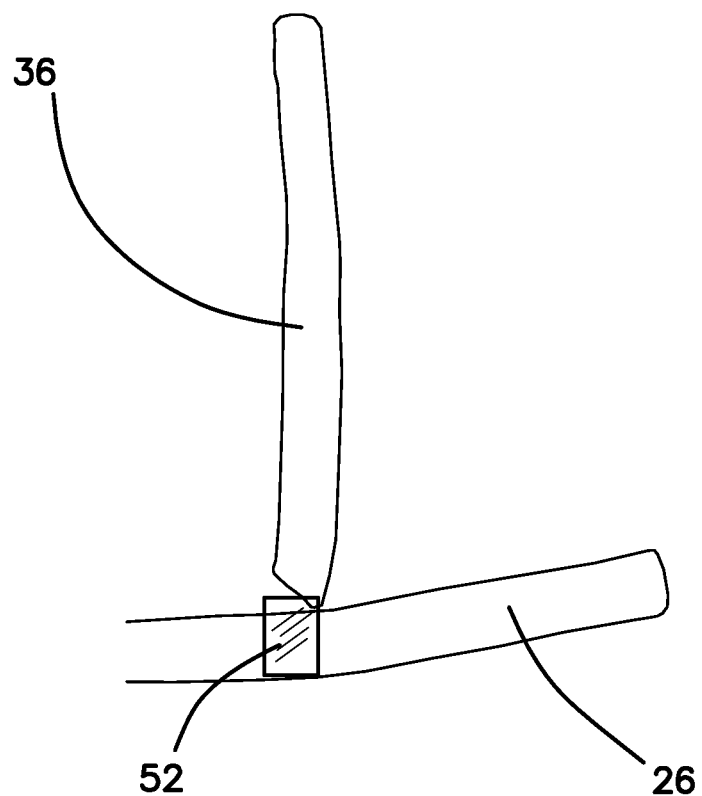
FIG. 5B is a top view of assembled portions of the renal hilum surgical simulation system in accordance with various embodiments of the present invention.

With reference to FIGS. 5A-B, a second vasculature subassembly is illustrated in accordance with various embodiments. As illustrated, the simulated renal artery 36 is adhered or otherwise attached to the simulated aorta 26 by a silicone-to-silicone adhesion and, in various embodiments, with consistent hard durometer silicone. In various embodiments, wet silicone is employed as an adhesive and allowed to cure to solidify the connection. The aorta adhesion area 52 is depicted by a rectangular box in FIG. 5B. In various embodiments, the simulated aorta 26 has a semi-cylindrical shape as seen for example in FIG. 14.

Figure 6:
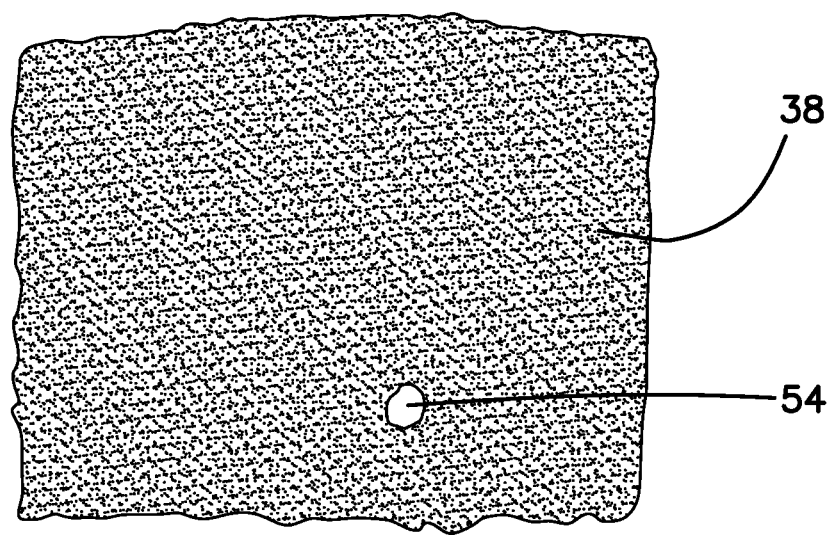
FIG. 6 is a top view of portions of the renal hilum surgical simulation system in accordance with various embodiments of the present invention.
Figure 7:
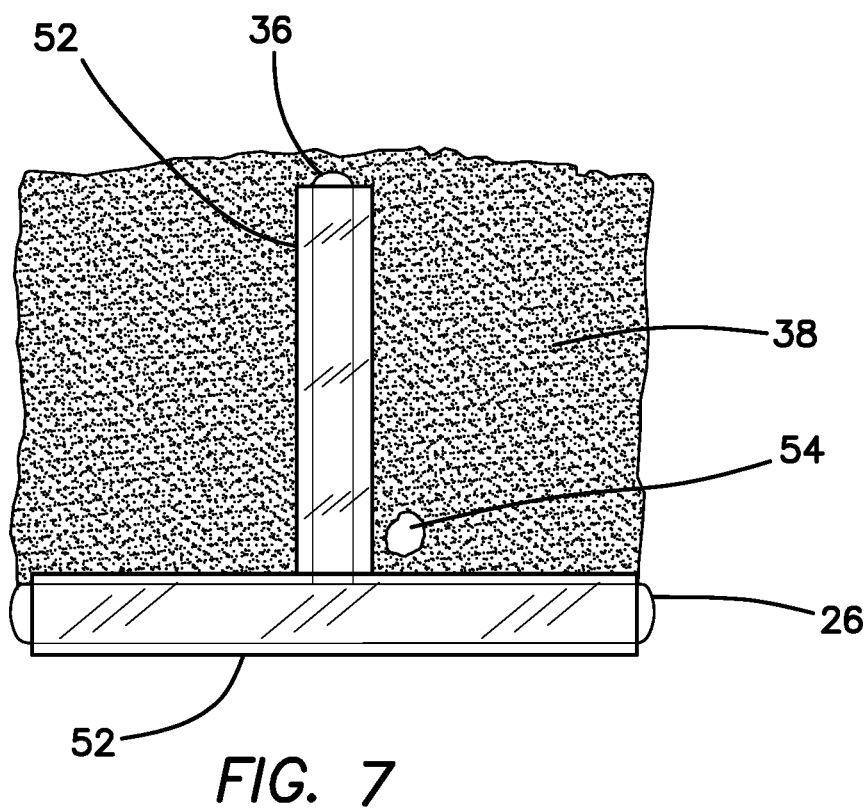
FIG. 7 is a top view of assembled portions of the renal hilum surgical simulation system in accordance with various embodiments of the present invention.

Turning now to FIG. 6, a back fibrous layer 38 is provided. The back fibrous layer 38 in various embodiments is made of or includes batting. In various embodiments, the back fibrous layer is a rectangular, substantially planar layer of polyfill or other fibrous material. The back fibrous layer 38 includes a hole or opening 54 through which the lumbar vein 32 is passed. The opening 54 is unique to the surgical simulation system 10 and is not anatomically correct. The second vasculature subassembly comprising the renal artery 36 and aorta 26 is adhered to the back or first fibrous layer 38 using adhesive as shown in FIG. 7. The adhesion area 52 is shown to be substantially under the entire second subassembly.

Figure 8:
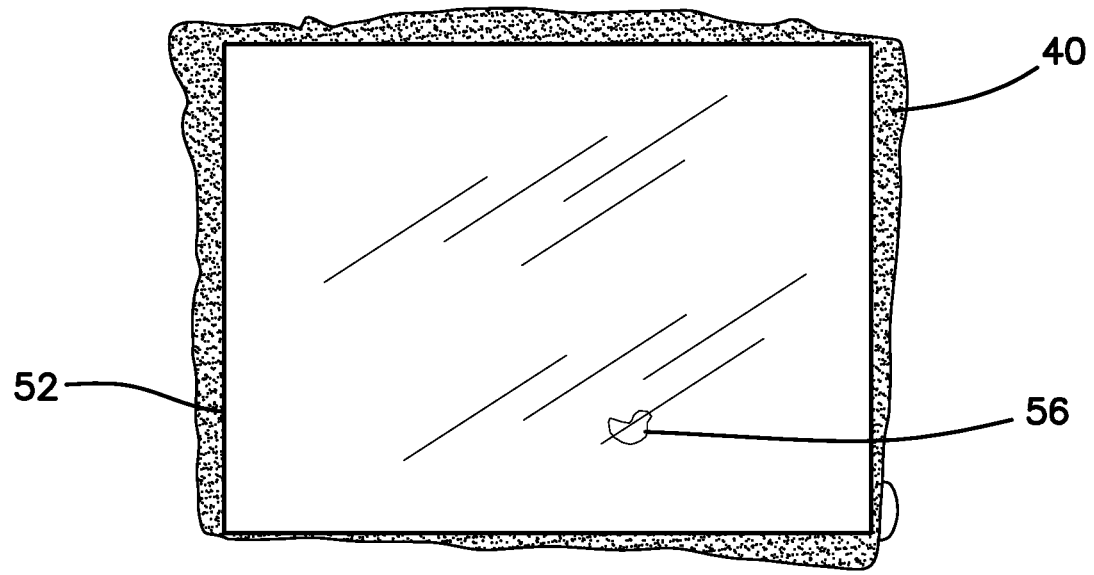
FIG. 8 is a top view of portions of the renal hilum surgical simulation system in accordance with various embodiments of the present invention.
Figure 9:
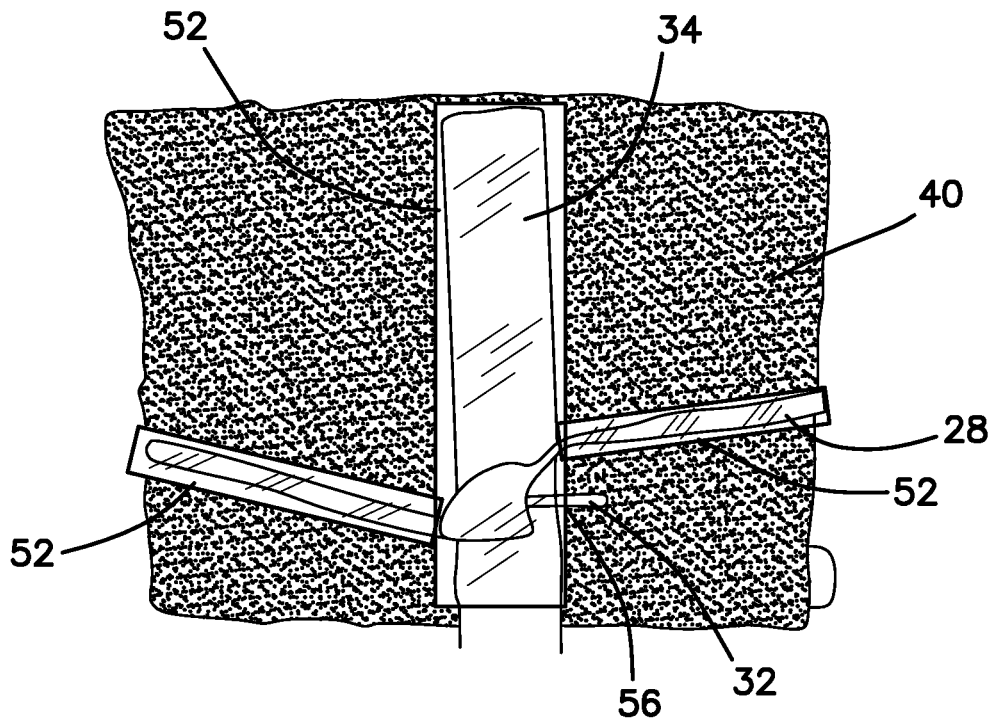
FIG. 9 is a top view of assembled portions of the renal hilum surgical simulation system in accordance with various embodiments of the present invention.

Turning now to FIG. 8, in accordance with various embodiments, a second fibrous layer 40 is adhered to the simulated renal artery 36 and aorta 26 of the second vasculature subassembly. The second fibrous layer 40 is made of or includes batting. In various embodiments, the second fibrous layer is a rectangular, substantially planar layer of polyfill or other fibrous material. The second fibrous layer 40 is also adhered to the back or first fibrous layer 38 with an adhesion area 52 indicated by the large rectangle. The second fibrous layer 40 also contains a hole or aperture 56 extending from the top and through to the bottom surface of the second fibrous layer 40. The simulated lumbar vein 32 passes through this hole 56 and the hole 54 in the back fibrous layer 38 and, as such, the holes 54, 56 are aligned when the layers are stacked such that their perimeters are substantially congruent to fit inside the pocket. Turning now to FIG. 9, the first vasculature assembly, comprising the simulated gonadal vein 28, adrenal vein 30, lumbar vein 32 and renal vein 34, are adhered to the second fibrous layer 40 with an adhesion area 52 being under the renal vein 34, adrenal vein 30 and gonadal vein 28 as shown in FIG. 9 with the adhesion area 52 shown by three rectangles. The simulated lumbar vein 32 is passed through the holes 56 and 54 in the fibrous layers 40, 38.

Figure 10:
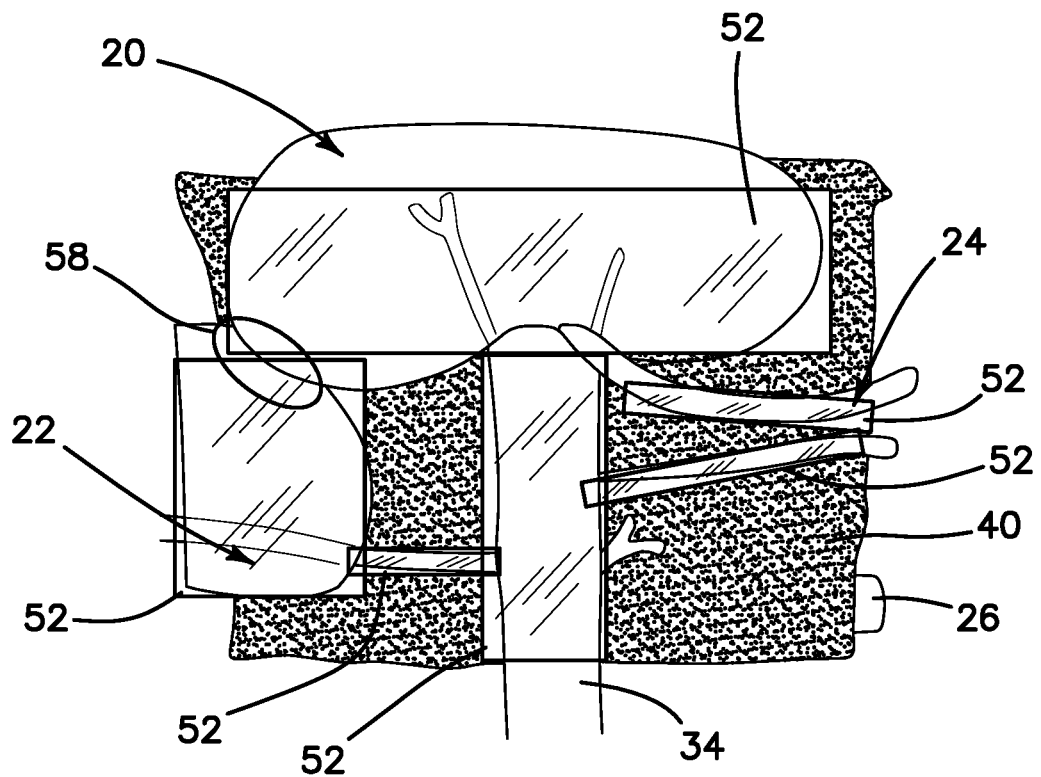
FIG. 10 is a top view of portions of the renal hilum surgical simulation system in accordance with various embodiments of the present invention.

Turning now to FIG. 10, the simulated kidney 20, ureter 24 and adrenal gland 22 are connected to the simulated renal vein 34 and adrenal vein 30 and to the second fibrous layer 40. The simulated ureter 24 is adhered to or otherwise attached to the back of the simulated kidney 20. The kidney 20 is adhered to the top end of the simulated renal vein 34 as well as the second fibrous layer 40. The simulated ureter 24 is adhered to the second fibrous layer 40. The simulated adrenal gland 22 is adhered to the simulated adrenal vein 30 as well as the second fibrous layer 40. The simulated adrenal gland 22 is not adhered to the simulated kidney 20. The adhesion areas 52 are demonstrated by the rectangular shapes in FIG. 10 and the non-adhesion area 58 between the adrenal gland 22 and the kidney is demonstrated by the ellipse in FIG. 10.

Figure 11:
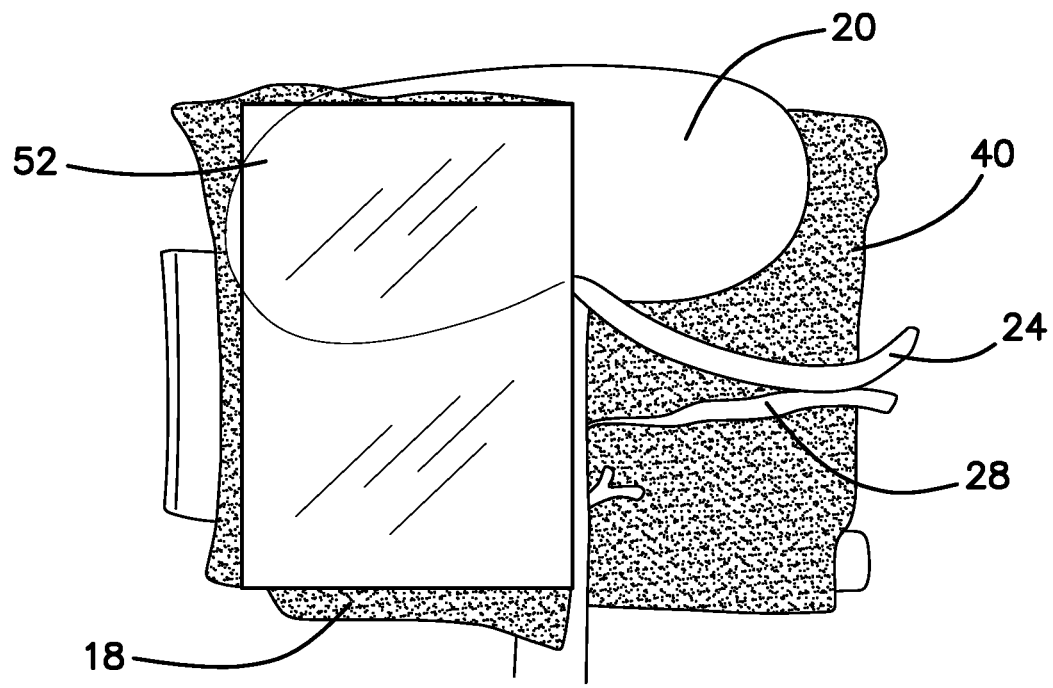
FIG. 11 is a top view of assembled portions of the renal hilum surgical simulation system in accordance with various embodiments of the present invention.

Turning now to FIG. 11, the half fibrous layer 18 is adhered to the simulated kidney 20, the simulated adrenal gland 22, the adrenal vein 30, the renal vein 34, and the second fibrous layer 40. The adhesion area 52 is shown by a rectangle substantially completely underneath the half fibrous layer 18. The half fibrous layer 18 is provided to simulate a denser dissectible areolar tissue found within a patient. In various embodiments, the half fibrous layer 18 is created from cutting the larger piece of fibrous material, e.g., batting, in half, length-wise and pulling apart the layers of the batting to create a thinner piece to add to the density of the dissectible tissue. In accordance with various embodiments, the fibers or fibrous material encapsulate and surround one or more or every simulated anatomical structure. The multiple layers of fibrous material, e.g., batting, provide varying density of dissectible material in which a surgeon has to navigate. As stated previously, the simulated lumbar vein 32 passes through the holes 54, 56 in the fibrous layers 38, 40. When the surgical simulation system 10 is flipped over, back side facing up, as shown in FIG. 12, the simulated lumbar vein 32 is pulled through the holes 54, 56 to expose it on the back side.

Figure 12:
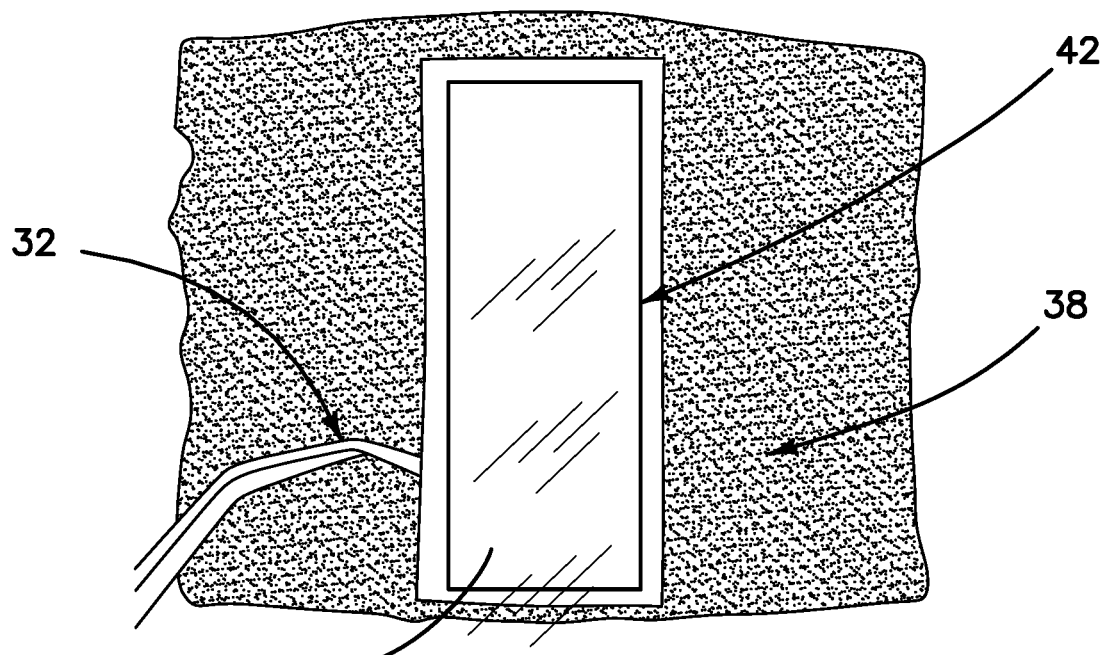
FIG. 12 is a top view of portions of the renal hilum surgical simulation system in accordance with various embodiments of the present invention.
Figure 13:
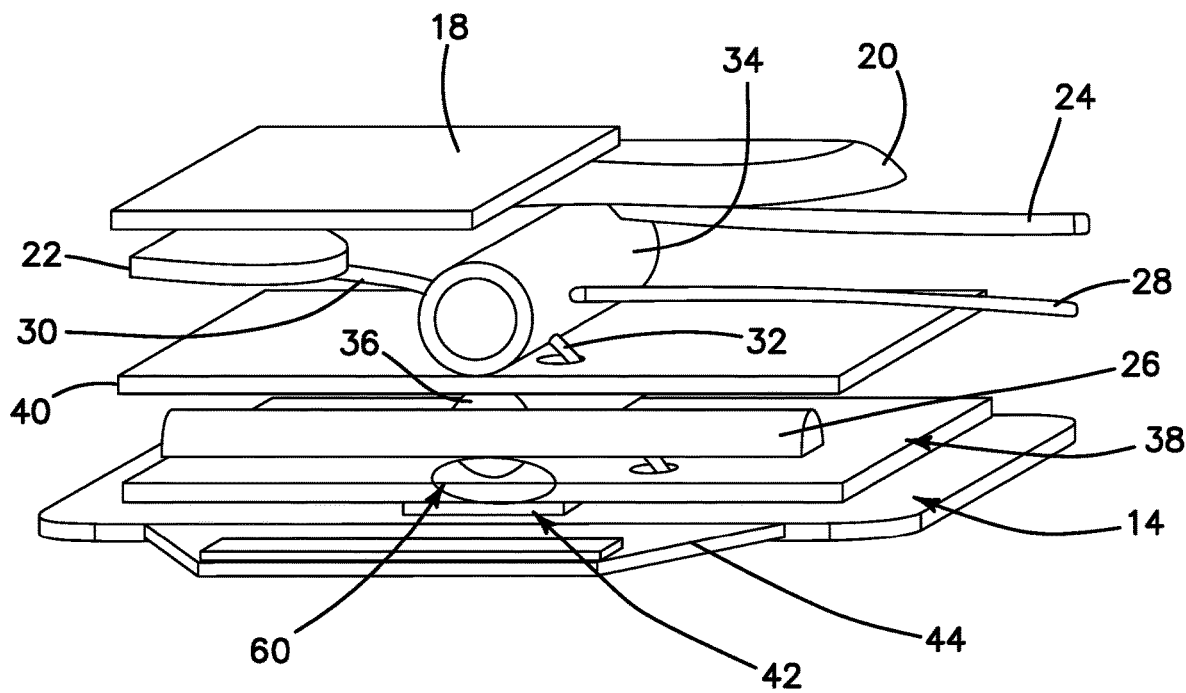
FIG. 13 is an exploded perspective view of the renal hilum surgical simulation system in accordance with various embodiments of the present invention.

With reference to FIGS. 12-13, the surgeon must circumferentially dissect around the renal vein 34. In accordance with various embodiments, the contents of the surgical simulation system 10 are encapsulated between the top silicone layer 12 and the bottom silicone layer 14. The bottom silicone layer 14 of the surgical simulation system 10, in various embodiments, is constructed of uncured silicone, which is adhered to the top fibrous layer 16 around the outside border, creating a pocket upon curing together with all of the components retained by and located inside the pocket. Because the bottom silicone layer 14 of silicone is uncured during manufacturing of the assembly, the back fibrous layer 38 will also adhere to the wet silicone. If the back fibrous layer 38 becomes too saturated with uncured silicone, it can undesirably start to adhere the simulated renal artery 36 and aorta 26 to the bottom silicone layer 14, which would prevent the ability of the surgeon trainee to circumferentially dissect around the renal artery of the simulated LDN procedure. To prevent or reduce this undesirable adhesion, an adhesion blocker 42 is used to ensure that the simulated renal artery 36 can be dissected circumferentially around as shown in FIG. 13 with the dissection area 60 demarked with a ellipse. The adhesion blocker 42, in various embodiments, is made of a silicone sheet, molded to the approximate thickness of the bottom silicone layer 14, and cut to the size of the renal artery 36 to prevent any undesired adhesion. In various embodiments, the adhesion blocker 42 is placed or used such that it does not obstruct the lumbar vein 32, since the lumbar vein 32 will ultimately be adhered to the back of the surgical simulation system 10, bottom silicone layer 14. The adhesion blocker 42, in various embodiments, is adhered to the back fibrous layer 38 shown, for example, by the rectangular adhesion area, without excess force applied, so as not to saturate the fibrous material, e.g., batting, through and adhere the simulated renal artery 36 or aorta 26.

Figure 14:
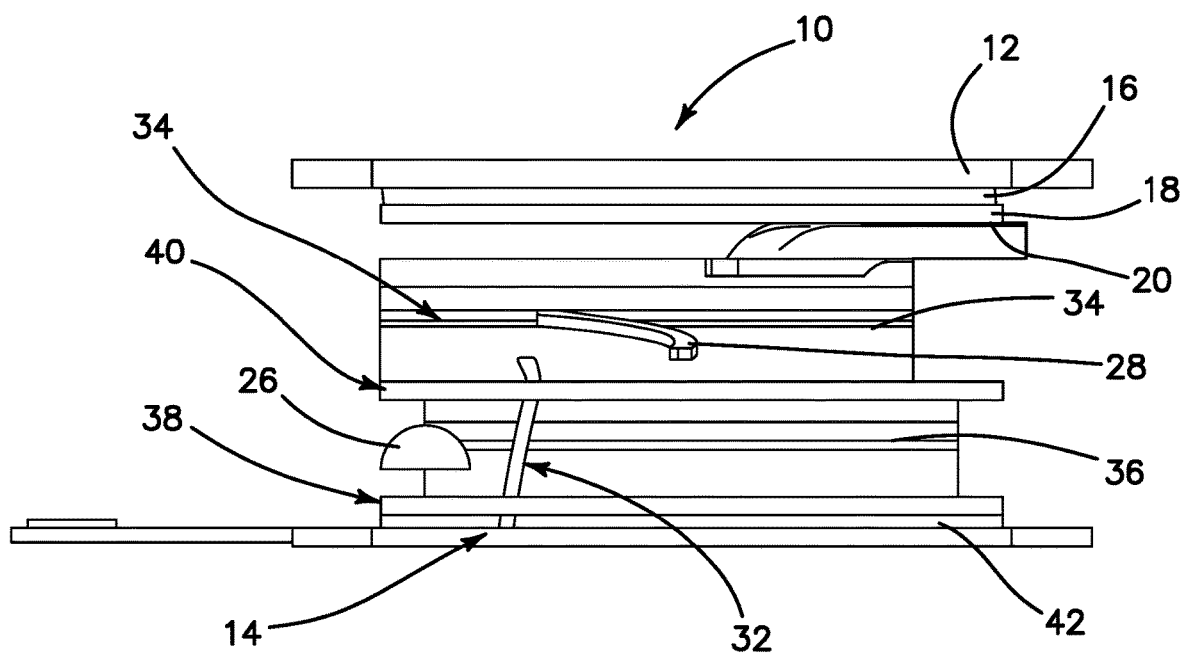
FIG. 14 is an exploded side view of the renal hilum surgical simulation system in accordance with various embodiments of the present invention.

With reference to FIG. 14, the simulated lumbar vein 32, in various embodiments, is adhered to the simulated renal vein 34 and then passes through the second fibrous layer 40 and back fibrous layer 38 and adhered to the bottom silicone layer 14. In accordance with various embodiments, the adherence of the lumbar vein 32 to the bottom silicone layer 14 occurs while the model or surgical simulation system contents are placed on the uncured bottom silicone layer 14. Upon curing of the bottom silicone layer 14, the contact of the lumbar vein 32 with the uncured bottom silicone layer 14 will form the necessary adhesion. In various other embodiments, the lumbar vein 32 is adhered to the second fibrous layer 40 and back fibrous layer 38 at their respective holes 56, 54.

In various embodiments, in the surgical simulation system, the layers are adhered together by intertwining the surrounding fibrous layers, holding simulated structures in place with or without the use of silicone or silicone adhesive.

In various embodiments, fibers of the fibrous, e.g., batting, layers are mesh through one another to create a knit matrix and/or when push through the silicone components a slight adhesion of batting to silicone is created. As such, adequate adhesion of tissue (e.g., batting) to the organs (e.g., silicone) for a surgeon to dissect through in the simulated procedure is provided. Such knit matrix can also avoid or reduce the use of silicone glue layers that can be difficult to control for consistency throughout the surgical simulation system or cause unwanted residues.

Figure 15:
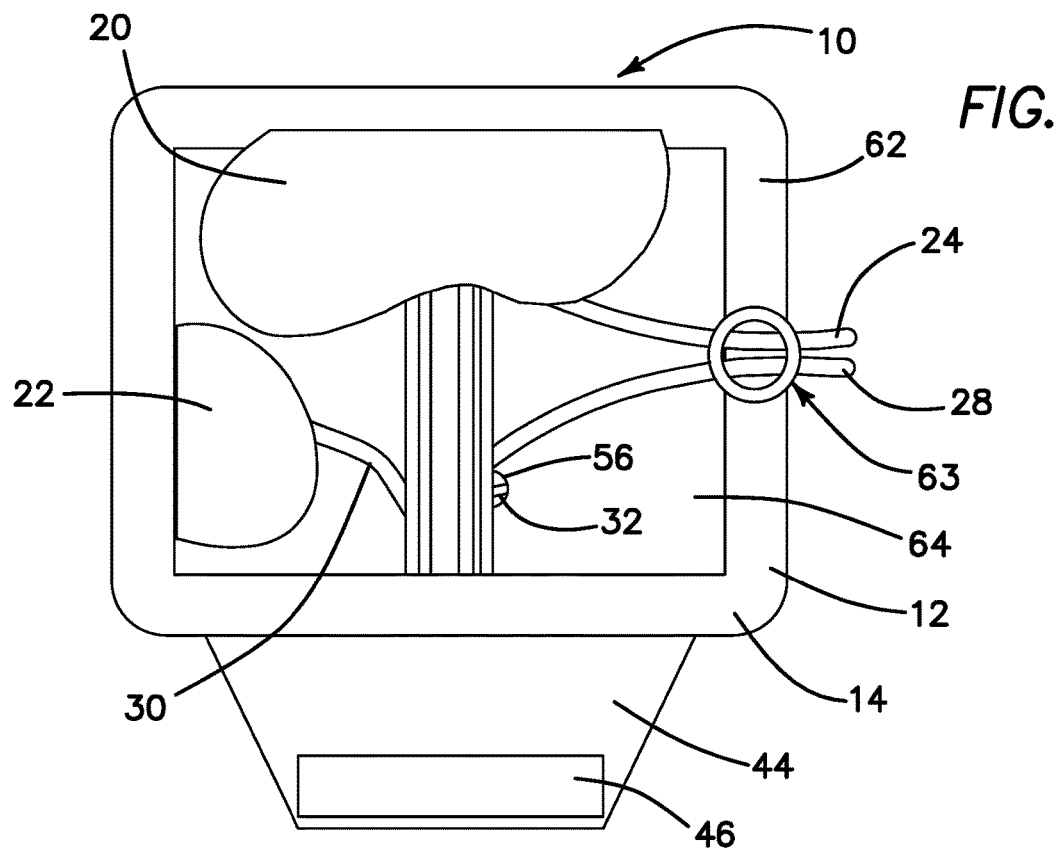
FIG. 15 is a top view of portions of the renal hilum surgical simulation system in accordance with various embodiments of the present invention.
Figure 16:
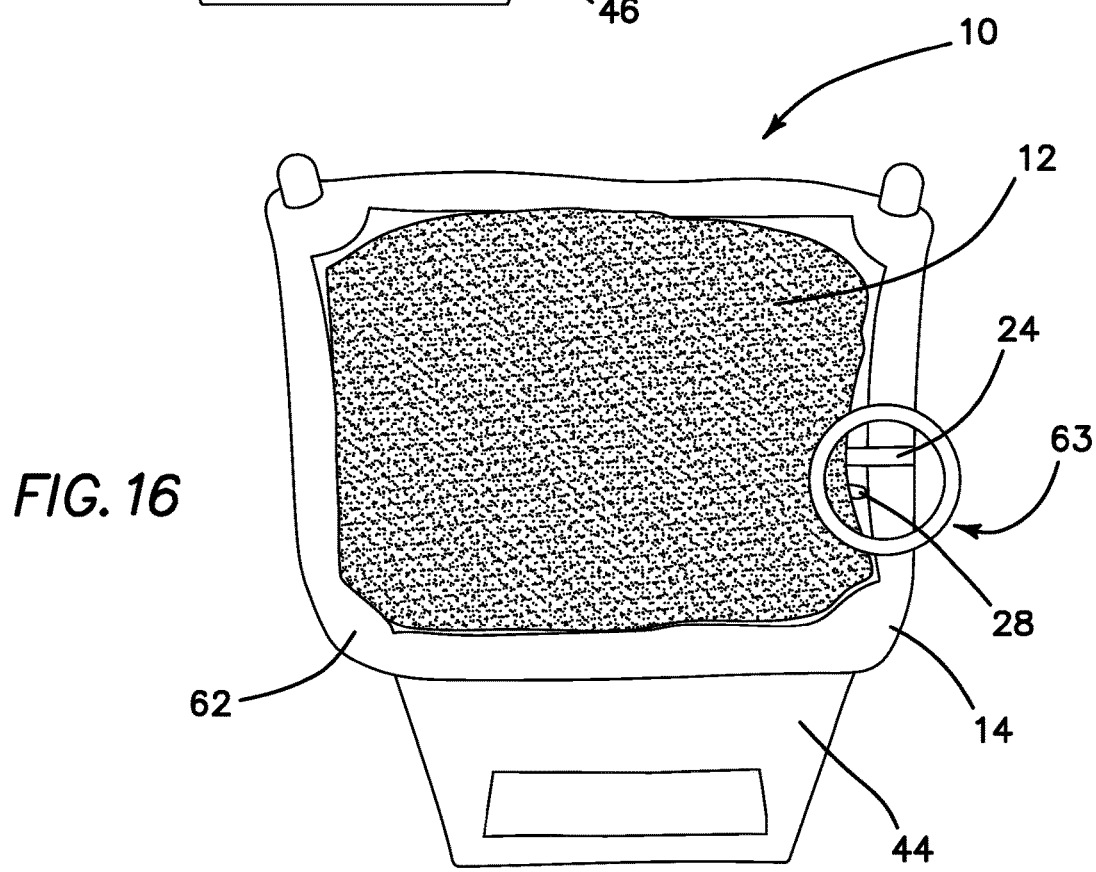
FIG. 16 is a top view of the renal hilum surgical simulation system in accordance with various embodiments of the present invention.

With reference now to FIGS. 15 and 16, in various embodiments, to ensure identification of the simulated ureter 24 and gonadal vein 28, the simulated ureter 24 and gonadal vein 28 are visible through the border/perimeter 62 of the surgical simulation system 10. In accordance with various embodiments, the border/perimeter 62 is formed by the top silicone layer 12 adhering together with the bottom silicone layer 14 to form a pocket 64. The simulated ureter 24 and gonadal vein 28 are visible through the top silicone layer 12 at the border/perimeter 62 of the surgical simulation system 10. These landmarks pose as an indicator as to where the surgeon should start dissection of the surgical simulation system 10. In order for these landmarks to be visible through the border 62, the simulated ureter 24 and gonadal vein 28 extend outwardly past the fibrous layers and into the border, highlighted by circle 63 in FIGS. 15-16. In various other embodiments, the color and/or opacity of the top silicone layer 12 is distinguished with respect to the simulated ureter 24 and gonadal vein 28 to allow for visibility of the landmarks through the top silicone layer 12.

Figure 17:
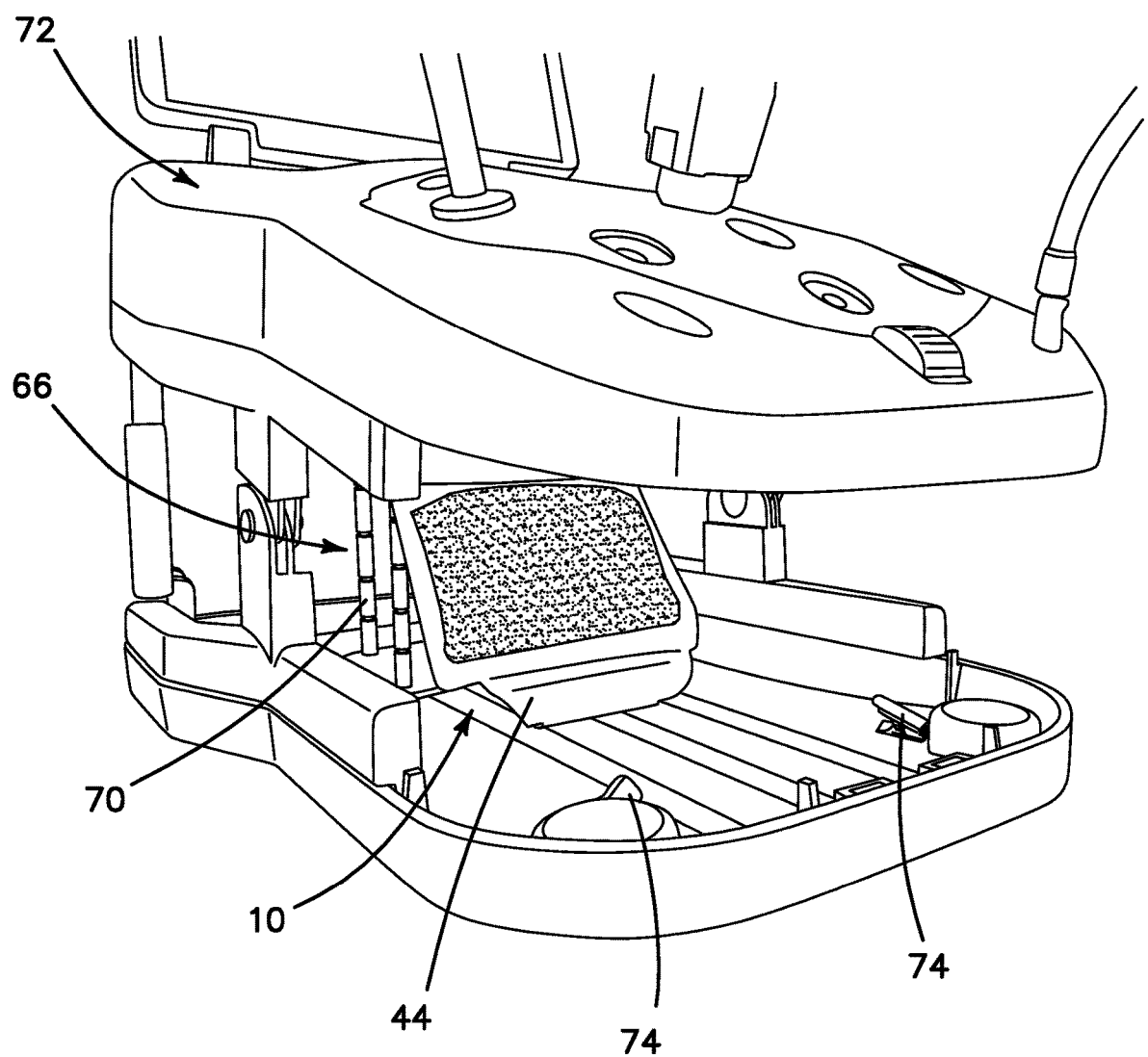
FIG. 17 is a perspective view of the renal hilum surgical simulation system in accordance with various embodiments of the present invention.
Figure 18:
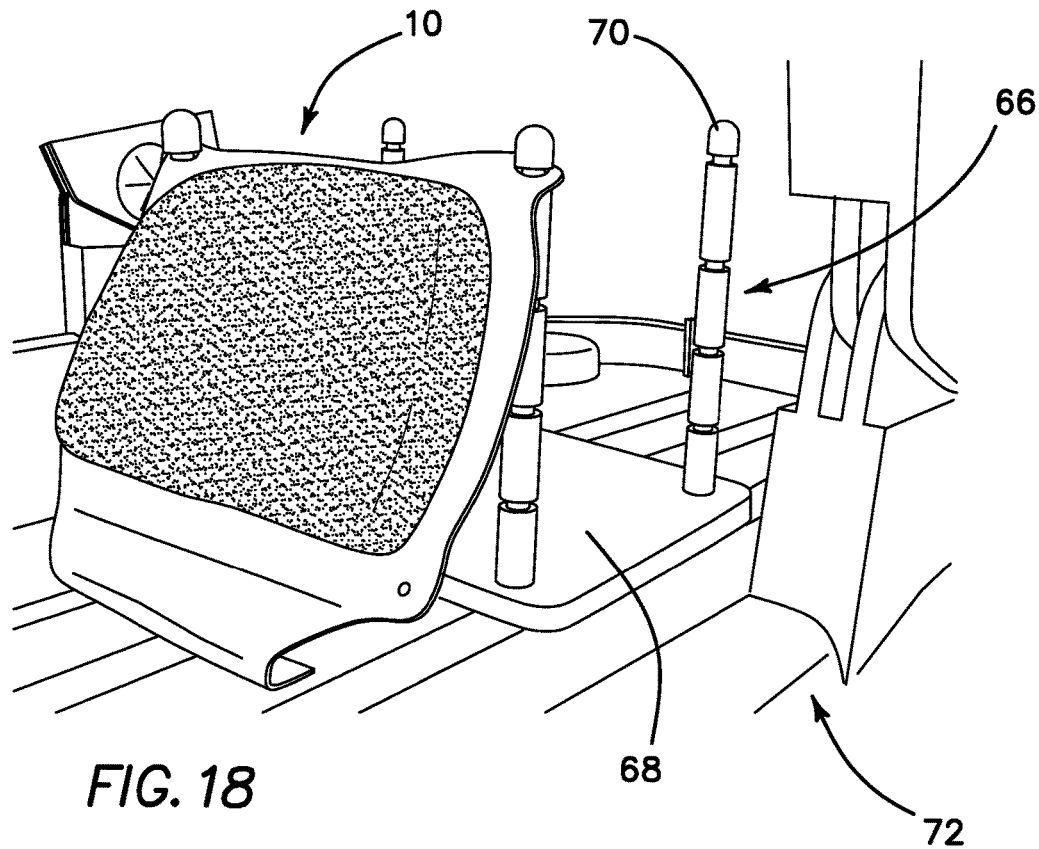
FIG. 18 is a perspective view of the renal hilum surgical simulation system in accordance with various embodiments of the present invention.
Figure 19:
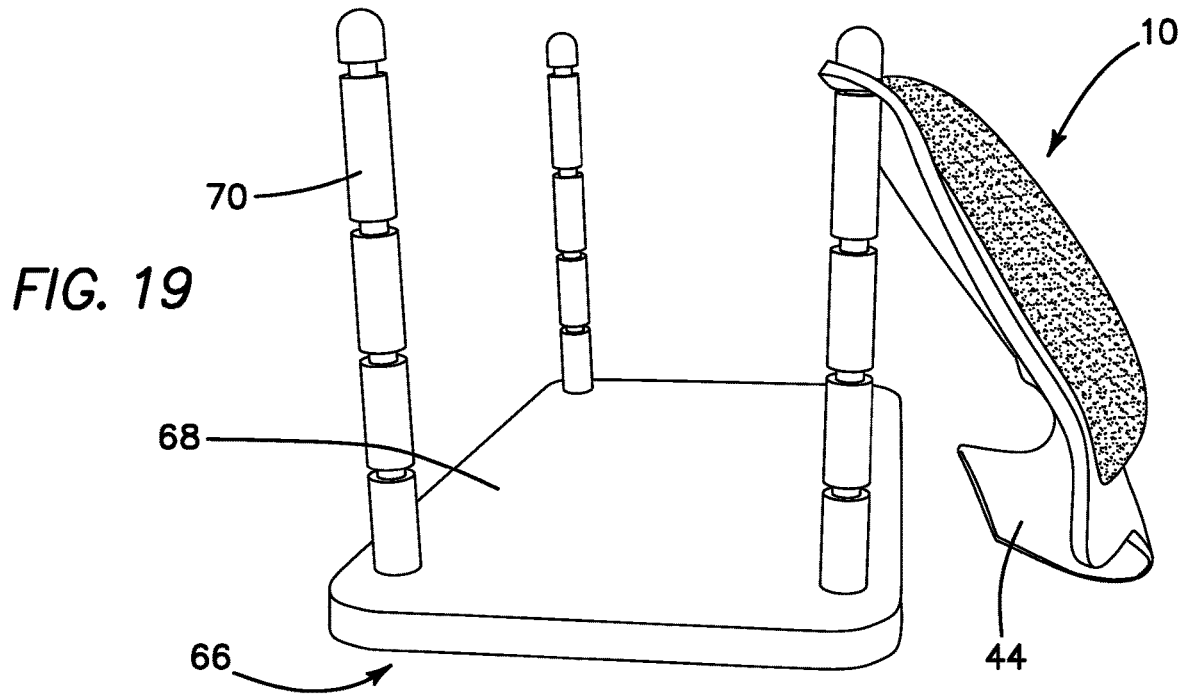
FIG. 19 is a side view of the renal hilum surgical simulation system in accordance with various embodiments of the present invention.

With reference to FIGS. 17-19, in accordance with various embodiments, the renal hilum dissection surgical simulation model 10 may include two or more holes along the border 62 for mounting on a stand 66 having a base 68 with at least two upstanding posts 70 extending upwardly from the base 68. The posts 70 are passed through the holes in the border 62. The stand 66 with the surgical simulation model 10 can then be located inside a cavity of a laparoscopic trainer 72 for the procedural practice to begin. The trainer defines a cavity between a top cover and a base. The cavity is obscured from direct view by the practitioner and a scope is inserted through the top cover to capture a live video feed of the cavity, which is displayed on a monitor to the practitioner. The practitioner or trainee inserts various instruments through the top cover and performs the simulated procedure on the surgical simulation system 10 inside the cavity. The stand 66 serves to support the surgical simulation model or system 10 inside the trainer 72. In various embodiments, the surgical simulation system 10 contains one or more holes or apertures in each of the top two corners of the border 62. These holes interface with the posts 70. In various embodiments, the stand 66 includes four posts 70. In various embodiments, the border 62 is made from elastic silicone material that stretches and returns to its original shape and the holes of the border are stretched to fit over the post 70 and then return to a tight fit to secure the surgical simulation system 10 into place on the posts 70 of the base 68. The placement of the holes on the posts 70, along with the angled position of a flap 44, allow for the surgical simulation system 10 to be placed in a variety of angles with respect to the base 68 that may be necessary to complete the simulated procedure. In various embodiments, in order to stabilize the upper corners of the surgical simulation system 10, clips 74 within the trainer 72 are used to pull the surgical simulation system upright and/or hold it in position. In accordance with various embodiments, a stand or stable structure and/or similar attachments to the surgical simulation system and/or the trainer may hold the surgical simulation system stable in an angled position for the simulated surgical procedure.

In various embodiments, the surgical simulation system includes, is integrated or is embedded with a frame that supports, suspends and/or angles the surgical simulation system and in various embodiments in order to replicate or simulate the angled position of a patient. The surgical simulation system is removably attached to the frame and in various embodiments, the frame is removably attached to a surgical trainer. In such embodiments, the apertures within the border and/or the additional portion provided by the border may be removed along with the flap, the associated attachment and/or the additional portions provided by the surgical simulation system providing the flap, attachment and/or border.

During an LDN procedure, the patient is situated lying down on their side with a slight backwards tilt. In order to replicate or simulate the angled position of a patient, the renal hilum dissection surgical simulation system 10, according to various embodiments, incorporates a flap 44 designed to be used as a support stand. Looped side of a hook-and-loop type fastener 46, such as VELCRO®, is adhered to the flap 44 and configured to mate with the opposite or hooked side of the hook-and-loop type fastener 46 located on the bottom floor of the trainer 72. The flap 44 extends from the bottom side of the surgical simulation system 10 and in various embodiments, is constructed a soft and flexible yet durable silicone that allows it to bend while maintaining its structural integrity. In various embodiments, the flap 44 is flexible so that two pieces of the hook-and-loop type fastener 46 can mate, while creating a bent stand for which to hold the surgical simulation system into the desired angle and position within the laparoscopic trainer 72. The flap 44 is used in conjunction with or without the stand 66. Attachment of the flap 44 to the floor of the trainer may vary and in various embodiments, the hook-and-loop type fastener may be replaced with or further include, for example, one or more snaps, magnets, posts or clips, and/or may extend through, attach to or be adhered to an intermediary component, e.g., an extension of base 68, between the attachment/surgical simulation system and the floor of the trainer. The attachment of the surgical simulation system allows the surgical simulation system to be removable and thus eases replace-ability, repositioning or reorientation of the surgical simulation system. Such attachment or positioning of the various portions of the surgical simulation system relative to the trainer ensures that the orientation or angled position of the surgical simulation system replicates the orientation or position of the patient and in various embodiments ensures the tactile feedback, flexibility or other features provided by the surgical simulation system are not sacrificed and/or the simulated LDN procedure compromised.

In various embodiments, other variations to the surgical simulation system 10 may include alteration of the anatomical structures inside the pocket to include abnormal, diseased, or varying anatomy. Such anatomy could include the right renal hilum or the inclusion of additional lumbar veins and/or tumors. In other embodiments, the surgical simulation system 10 is dipped or soaked in water or other liquid to better represent the environment of a patient. For example, when the fibrous or batting layers become saturated with liquid they tend to become denser and more adhered. This allows, in various embodiments, for more applicable and accurate representation of the difficulty of the LDN procedure. Instead of a liquid such as water, the pocket 64 could also be filled with a gel like substance.

In various embodiments, the arrangement and/or composition of the various portions and components are provided to vary the difficulty of the surgical simulation system and thereby vary the simulated surgical procedure to enhance surgical training and surgical skill assessment. Such examples are described throughout the description and provided in the claims that may seem arbitrary but again are included or excluded to vary and adjust the difficulty the surgical simulation system to enhance surgical training and skill assessment. Some of these examples can include varying fibrous layer densities, exaggerating or underplaying simulated renal vasculature and/or organ shapes, dimensions and/or tactile response, saturating fibrous layers with liquid, creating simulated vasculature paths, e.g., a simulated renal vasculature threaded or extended through at least one opening in one or more or different fibrous layers, and/or varying the coloring and/or composition of the simulated renal vasculature, organs and/or surrounding structures.

In various embodiments, both sides or layers of the surgical simulation system are penetrable to ensure or further assess surgical skill such that if mishandling or manipulation of the simulated tissue, e.g., too much force is used, a noticeable puncture or opening in the opposing side of the surgical simulation system would be visible. Likewise, the thickness or distance between the layers are minimal, e.g., a fraction of the length or width of the surgical simulation system or the pocket contained therein, to further test or enhance the assessment of the surgical skill or effective operation of the simulated surgical procedure.

In various embodiments, the surgical simulation system is so confined to limit the working space available to simulate the surgical procedures. Likewise, the size of the pocket, for example, can be modified to further limit the operational space and thereby increase the difficulties of the simulated surgical procedure. Additionally, the number and/or size of the components and combinations thereof are further limited to enhance portability of the surgical simulation system, operation within a trainer, e.g., a portable laparoscopic trainer and/or further focus the surgical trainee on the specific simulated procedure. Similarly, omitted features or reduction of sizes or shapes are provided to enhance the surgical simulation system, e.g., increase difficulties or focus on the specific simulated surgical procedure, even though such differences or changes may not be anatomically correct. In various embodiments, the surgical simulation system includes at least one simulated renal vasculature, e.g., renal vein, renal artery, and/or the like and/or other vasculature/ vessels provided herein, and/or at least one simulated renal organ, e.g., adrenal gland, kidney and/or the like and/or other organs/glands provided herein.

The above description is provided to enable any person skilled in the art to make and use the surgical simulation system or systems and perform the methods described herein and sets forth the best modes contemplated by the inventors of carrying out their inventions. Various modifications, however, will remain apparent to those skilled in the art. It is contemplated that these modifications are within the scope of the present disclosure. Different embodiments or aspects of such embodiments may be shown in various figures and described throughout the specification. However, it should be noted that although shown or described separately each embodiment and aspects thereof may be combined with one or more of the other embodiments and aspects thereof unless expressly stated otherwise. It is merely for easing readability of the specification that each combination is not expressly set forth.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A renal hilum surgical simulation system comprising:
a first penetrable layer having an upper and lower surface;
a second penetrable layer having an upper and lower surface, a periphery of the upper surface of the second penetrable layer connected to a periphery of the lower surface of the first penetrable layer;
a pocket disposed between the first and second penetrable layers, the pocket being delimited and encased by the peripheries of the first and second penetrable layers connected together;
a plurality of fibrous layers disposed between the first and second penetrable layers;
a plurality of simulated renal vasculature disposed between the plurality of fibrous layers and enclosed within the pocket; and
an adhesion blocker disposed on the second penetrable layer, wherein the adhesion blocker is configured to prevent adhesion between the at least one simulated renal vasculature and the second penetrable layer.

2. The system of claim 1 wherein at least one of the plurality of simulated renal vasculature extends through the plurality of fibrous layers.

3. The system of claim 2 wherein the at least one of the plurality of simulated renal vasculature extends through an aperture disposed in at least one of the plurality of fibrous layers.

4. The system of claim 3 wherein at least one of the plurality of simulated renal vasculature extends through a first aperture disposed in a first fibrous layer of the plurality of fibrous layers and a second aperture disposed in a second fibrous layer of the plurality of fibrous layers.

5. The system of claim 4 wherein at least one of the plurality of simulated renal vasculature has a semi-cylindrical shape.

6. The system of claim 1 wherein a first simulated renal vasculature of the at least one of the plurality of simulated renal vasculature extends along a width of the pocket and a second simulated renal vasculature of the at least one of the plurality of the simulated renal vasculature extends perpendicular to the first simulated renal vasculature and along a length of the pocket.

7. The system of claim 1 wherein the at least one simulated renal vasculature includes at least one notch disposed on an upper portion of the at least one simulated renal vasculature and at least one notch disposed on a lower portion of the at least one simulated renal vasculature.

8. The system of claim 1 wherein at least one of the plurality of fibrous layers is a water saturated fibrous layer.

9. The system of claim 1 wherein at least one of the plurality of fibrous layers is a multi-layered silicone batting.

10. The system of claim 1 wherein at least one of the plurality of fibrous layers includes a first fibrous layer having a width and length equal to a width and length of the pocket and a second fibrous layer adhered to the first fibrous layer, the second fibrous layer having a width and length half of the width and length of the pocket.

11. The system of claim 1 wherein the at least one simulated renal vasculature includes a first simulated renal vasculature and a second simulated renal vasculature, the first simulated renal vasculature being more puncture resistant than the second simulated renal vasculature.

12. The system of claim 1 wherein the at least one simulated renal vasculature includes a first simulated renal vasculature and a second simulated renal vasculature, wherein the first simulated renal vasculature is adhered to the second simulated renal vasculature, and wherein to the second simulated renal vasculature is adhered to a fibrous layer of the plurality of fibrous layers.

13. The system of claim 1, wherein at least one of the plurality of simulated renal vasculatures is configured to be circumferentially dissected.

14. The system of claim 1, wherein the adhesion blocker comprises a silicone sheet having a thickness corresponding to a thickness of the second penetrable layer.

15. The system of claim 1, wherein the adhesion blocker is sized to a corresponding size of the at least one simulated renal vasculature.

16. A renal hilum surgical simulation system comprising:
a first penetrable layer having an upper and lower surface;
a second penetrable layer having an upper and lower surface, a periphery of the upper surface of the second penetrable layer connected to a periphery of the lower surface of the first penetrable layer;
a pocket disposed between the first and second penetrable layers, the pocket being delimited and encased by the peripheries of the first and second penetrable layers connected together;
a plurality of fibrous layers disposed between the first and second penetrable layers;
a plurality of simulated renal vasculature disposed between the plurality of fibrous layers and enclosed within the pocket;
wherein the at least one simulated renal vasculature includes a plurality of notches spaced from each other.

17. The system of claim 16 wherein the plurality of fibrous layers further comprises a plurality of fibrous layers having varying densities.

18. The system of claim 1 wherein the plurality of fibrous layers further comprises:
a first fibrous layer connected to the lower surface of the first penetrable layer;
a second fibrous layer connected to the first fibrous layer and unconnected to the first penetrable layer, the first fibrous layer disposed between the first penetrable layer and the second fibrous layer and spacing the second fibrous layer from the first penetrable layer; and a third fibrous layer disposed between the second penetrable layer and the at least one simulated renal vasculature.

19. The system of claim 18 wherein the plurality of fibrous layers further comprises a fourth fibrous layer including an aperture aligned with an aperture in the third fibrous layer, a portion of the at least one simulated renal vasculature extending through the aperture of the third fibrous layer and the aperture of the fourth fibrous layer.

20. A renal hilum surgical simulation system comprising:

a first penetrable layer having an upper and lower surface;

a second penetrable layer having an upper and lower surface, a periphery of the upper surface of the second penetrable layer connected to a periphery of the lower surface of the first penetrable layer;

a pocket disposed between the first and second penetrable layers, the pocket being delimited and encased by the peripheries of the first and second penetrable layers connected together; and a plurality of fibrous layers disposed between the first and second penetrable layers;

a plurality of simulated renal vasculature disposed between the plurality of fibrous layers and enclosed within the pocket;

wherein the at least one simulated renal vasculature further comprises a first simulated renal vasculature and a second simulated renal vasculature, and wherein at least one of the plurality of fibrous layers is disposed between the first simulated renal vasculature and the second simulated renal vasculature.

* * * * *